(12) United States Patent
Ekman et al.

(10) Patent No.: US 9,474,859 B2
(45) Date of Patent: *Oct. 25, 2016

(54) AUTO-INJECTOR

(75) Inventors: Matthew Ekman, Macclesfield (GB); Simon Francis Brereton, Cambridge (GB); Thomas Mark Kemp, Ashwell (GB)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 882 days.

This patent is subject to a terminal disclaimer.

(21) Appl. No.: 13/807,445

(22) PCT Filed: Jun. 22, 2011

(86) PCT No.: PCT/EP2011/060502
§ 371 (c)(1),
(2), (4) Date: Jul. 12, 2013

(87) PCT Pub. No.: WO2012/000871
PCT Pub. Date: Jan. 5, 2012

(65) Prior Publication Data
US 2013/0296795 A1 Nov. 7, 2013

Related U.S. Application Data

(60) Provisional application No. 61/413,782, filed on Nov. 15, 2010.

(30) Foreign Application Priority Data

Jun. 28, 2010 (EP) .................................. 10167478

(51) Int. Cl.
*A61M 5/32* (2006.01)
*A61M 5/20* (2006.01)

(52) U.S. Cl.
CPC .......... *A61M 5/2033* (2013.01); *A61M 5/326* (2013.01); *A61M 2005/206* (2013.01); *A61M 2005/2013* (2013.01); *A61M 2005/2086* (2013.01); *A61M 2005/3247* (2013.01); *A61M 2205/581* (2013.01); *A61M 2205/582* (2013.01); *Y10T 74/18984* (2015.01)

(58) Field of Classification Search
CPC .................... A61M 5/326; A61M 2005/2013; A61M 2005/206; A61M 2005/2086; A61M 2005/3247; A61M 2205/581; A61M 2205/582; A61M 5/2033; Y10T 4/18984
USPC ......................................................... 604/197
See application file for complete search history.

(56) References Cited

U.S. PATENT DOCUMENTS

| 2,591,457 | A | * | 4/1952 | Maynes | ............. | A61M 5/2033 |
| | | | | | | 604/137 |
| 5,026,349 | A | * | 6/1991 | Schmitz | ............. | A61M 5/2033 |
| | | | | | | 604/130 |
| 2002/0095120 | A1 | | 7/2002 | Larsen et al. | | |
| 2005/0222539 | A1 | | 10/2005 | Gonzales et al. | | |

FOREIGN PATENT DOCUMENTS

| EP | 1728529 A1 | 6/2006 |
| WO | 2009040605 A1 | 4/2009 |

* cited by examiner

*Primary Examiner* — Jason Flick
(74) *Attorney, Agent, or Firm* — Fish & Richardson P.C.

(57) ABSTRACT

The invention refers to a shuttering mechanism for controlling translation of a longitudinally moveable component within an elongate housing, the shuttering mechanism comprising at least one set of castellations on the housing and at least one resilient arm associated with the longitudinally moveable component, the resilient arm having a dog resiliently biased towards the castellations so as to engage between or behind the castellations and block the translation, wherein a respective shutter arm is arranged alongside the set of castellations, the shutter arm having a number of consecutive ramped protrusions spaced from each other, wherein the castellations and the ramped protrusions have the same pitch, wherein a profiled surface is formed by the castellations and the ramped protrusions, wherein the shutter arm is moveable in longitudinal direction with respect to the set of castellations, wherein the shutter arm has at least one locking position with its ramped protrusions essentially in phase with the castellations thus allowing the dog of the resilient arm to catch between or behind the castellations and wherein the shutter arm has at least one unlocking position with its ramped protrusions out of phase with the castellations in such a manner that the ramped protrusions prevent the dog from engaging with the castellations or disengage them thus allowing translation of the longitudinally moveable component.

15 Claims, 3 Drawing Sheets

AUTO-INJECTOR

CROSS REFERENCE TO RELATED APPLICATIONS

The present application is a U.S. National Phase Application pursuant to 35 U.S.C. §371, of International Application No. PCT/EP2011/060502, filed Jun. 22, 2011,, which claims priority to European Patent Application No. 10167478.6, filed Jun. 28, 2010, and U.S. Patent Application No. 61/413,782, filed Nov. 15, 2010. The entire disclosure contents of these applications are herewith incorporated by reference into the present application.

FIELD OF INVENTION

The invention relates to a shuttering mechanism for controlling translation of a longitudinally moveable component within an elongate housing, in particular for application in an auto-injector for delivering a dose of a liquid medicament.

BACKGROUND

Administering an injection is a process which presents a number of risks and challenges for users and healthcare professionals, both mental and physical.

Injection devices (i.e. devices capable of delivering medicaments from a medication container) typically fall into two categories—manual devices and auto-injectors.

In a manual device—the user must provide the mechanical energy to drive the fluid through the needle. This is typically done by some form of button/plunger that has to be continuously pressed by the user during the injection. There are numerous disadvantages for the user from this approach. If the user stops pressing the button/plunger then the injection will also stop. This means that the user can deliver an underdose if the device is not used properly (i.e. the plunger is not fully pressed to its end position). Injection forces may be too high for the user, in particular if the patient is elderly or has dexterity problems.

The extension of the button/plunger may be too great. Thus it can be inconvenient for the user to reach a fully extended button. The combination of injection force and button extension can cause trembling/shaking of the hand which in turn increases discomfort as the inserted needle moves.

Auto-injector devices aim to make self-administration of injected therapies easier for patients. Current therapies delivered by means of self-administered injections include drugs for diabetes (both insulin and newer GLP-1, class drugs), migraine, hormone therapies, anticoagulants etc.

Auto-injectors are devices which completely or partially replace activities involved in parenteral drug delivery from standard syringes. These activities may include removal of a protective syringe cap, insertion of a needle into a patient's skin, injection of the medicament, removal of the needle, shielding of the needle and preventing reuse of the device. This overcomes many of the disadvantages of manual devices. Forces required of the user/button extension, handshaking and the likelihood of delivering an incomplete dose are reduced. Triggering may be performed by numerous means, for example a trigger button or the action of the needle reaching its injection depth. In some devices the energy to deliver the fluid is provided by a spring.

Auto-injectors may be disposable or single use devices which may only be used to deliver one dose of medicament and which have to be disposed of after use. Other types of auto-injectors may be reusable. Usually they are arranged to allow a user to load and unload a standard syringe. The reusable auto-injector may be used to perform multiple parenteral drug deliveries, whereas the syringe is disposed after having been spent and unloaded from the auto-injector. The syringe may be packaged with additional parts to provide additional functionality.

US 2002/0095120, A1, discloses an automatic injection device which automatically injects a pre-measured quantity of fluid medicine when a tension spring is released. The tension spring moves an ampoule and the injection needle from a storage position to a deployed position when it is released. The content of the ampoule is thereafter expelled by the tension spring forcing a piston forward inside the ampoule. After the fluid medicine has been injected, energy stored in the tension spring is released and the injection needle is automatically retracted back to its original storage position.

SUMMARY

It is an object of the present invention to provide a novel means for controlling translation of a longitudinally moveable component within an elongate housing, e.g. movement of a plunger within the housing of an auto-injector.

The object is achieved by a shuttering mechanism according to claim 1.

Preferred embodiments of the invention are given in the dependent claims.

In the context of this specification the term proximal refers to the direction pointing towards the patient during an injection while the term distal refers to the opposite direction pointing away from the patient.

According to the invention a shuttering mechanism for controlling translation of a longitudinally moveable component within an elongate housing comprises at least one set of castellations on the housing, preferably on an inner surface and at least one resilient arm associated with the longitudinally moveable component. The resilient arm has a dog resiliently biased towards the castellations so as to engage between or behind the castellations and block the translation. A respective shutter arm is arranged alongside the set of castellations, the shutter arm having a number of consecutive ramped protrusions spaced from each other. The castellations and the ramped protrusions have the same pitch. A profiled surface is formed by the castellations and the ramped protrusions. The shutter arm is moveable in longitudinal direction with respect to the set of castellations. The shutter arm has at least one locking position with its ramped protrusions essentially in phase with the castellations thus allowing the dog of the resilient arm to catch between or behind the castellations. Furthermore the shutter arm has at least one unlocking position with its ramped protrusions out of phase with the castellations in such a manner that the ramped protrusions prevent the dog from engaging with the castellations or disengage them so the dog of the resilient arm may travel along the surface without catching behind the castellations. This allows translation of the longitudinally moveable component. The ramps of the ramped protrusions are arranged to push the dog away from behind or between the castellations upon translation of the shutter arm into the unlocked position.

When the longitudinally moveable component, e.g. a plunger of an auto-injector is translated the dog follows the profiled surface. Due to the ramped protrusions this surface is uneven thus providing an audible and tactile feedback to a user that the component is moving or that an injection is taking place, respectively. The motion can be paused by shifting the shutter arm into the locking position during translation of the longitudinally moveable component. Thus an injection or needle insertion may be paused and restarted if the user is finding the injection too fast or painful. Furthermore an injection may be prematurely halted without releasing the entire dose of medicament in the auto-injector.

The shuttering mechanism is preferably applied in an auto-injector for administering a dose of a liquid medicament, the auto-injector having a distal end and a proximal end with an orifice intended to be applied against an injection site and comprising:

an elongate housing arranged to contain a syringe with a hollow needle and a stopper for sealing the syringe and displacing the medicament, wherein the syringe is slidably arranged with respect to the housing, a drive means capable of, upon activation:

pushing the needle from a retracted position into an advanced position through the orifice and past the proximal end, and operating the syringe to supply the dose of medicament, a plunger for transmitting power from the drive means to the syringe and/or stopper, and activating means arranged to lock the drive means in a compressed state prior to manual operation and capable of, upon manual operation, releasing the drive means for injection.

The shuttering mechanism is arranged as the activating means and for controlling translation of the plunger being the longitudinally moveable component. The resilient arm of the shuttering mechanism is a plunger arm attached to the plunger.

In a preferred embodiment of the invention the shutter arm is connected to a sheath, telescoped within the proximal end of the housing and arranged to protrude proximally from the housing at least in an initial position in an as delivered state of the auto-injector. In the initial position of the sheath the shutter arm is in the locking position. From the initial position the sheath may be translated in distal direction into a triggering position thereby shifting the shutter arm into the unlocking position. This occurs when the user presses the proximal end of the auto-injector against an injection site, i.e. the skin of a patient. Thus the dog of the plunger arm comes clear of the castellations and the plunger is translated under load of the drive means so needle insertion and injection can take place.

In another preferred embodiment a syringe carrier is arranged inside the housing for holding the syringe. The syringe carrier is slidable with respect to the housing and comprises at least one clip locking it to the housing in a distal position in order to prevent relative axial motion of the syringe carrier. The sheath is arranged to disengage the clip upon translation in distal direction before the shutter arm reaches its unlocking position thus allowing the syringe carrier to move in proximal direction. The syringe is thus locked before triggering so the needle cannot be exposed unintentionally. If the auto-injector is removed from the injection site before the shutter arm reaches the unlocking position the clip can re-engage so the syringe is locked in a safe position again.

The sheath and the shutter arms may be connected by at least one resilient beam in a manner to allow the sheath to be moved away from the shutter arms by a defined maximum distance. This allows the sheath to move out of the housing even if the auto-injector is removed from the injection site mid-injection. In this case the shutter arms would be caught by the plunger arms. The resilient beam allows enough translation of the sheath to cover the needle, so the auto-injector is needle safe.

A spring may be arranged for biasing the sheath in proximal direction, so the sheath does not translate in distal direction unintentionally and is pushed into the needle safe position automatically.

The sheath spring is preferably arranged to bias the sheath against the syringe carrier. The sheath spring is thus compressed during needle insertion by the advancing syringe carrier so it is able to push the sheath beyond the initial position for covering the needle after the injection.

The sheath is preferably engaged with the syringe carrier in a manner to allow a maximum distance between the sheath and the syringe carrier so that a maximum proximal position of the sheath is restricted by the longitudinal position of the syringe carrier thus allowing the sheath to move proximally beyond its position of the initial state when the syringe carrier is proximal from its distal position. As long as the syringe carrier is engaged with the housing by the clip in its distal position the sheath is prevented from translating further than the initial position.

At least one snap may be provided near the proximal end of the housing for preventing the sheath from translating back in distal direction when the sheath has moved into a locking position proximally beyond its initial position, where the needle is covered post injection. The engagement of the sheath with the needle carrier prevents the sheath from locking behind the snap before triggering.

In a preferred embodiment the drive means is a compression spring grounded distally in the housing and bearing against the plunger.

A rotating damper may be arranged between the compression spring and a thrust plate at a distal end of the plunger. The rotating damper may have a cam arranged in a cam track on an inner surface of the housing, the cam track having at least one helical section for forcing the rotating damper to rotate upon axial translation under load of the compression spring thus generating friction between the rotating damper and the thrust plate. This allows for controlling the speed of the advancing plunger since the load of the drive spring is shared between the plunger and the friction. The amount of friction can be controlled by the pitch of the cam. This pitch can vary over the length of the helical section thus compensating for the decay in force with increasing expansion of the compression spring.

In yet another embodiment the cam track may have a straight section for preventing rotation of the rotating damper during needle insertion. Fast needle insertion and slow injection is thought to be less painful for a patient.

The injection may be paused by slightly reducing pressure on the sheath so the shutter arm translates by a small distance in proximal direction so the ramped protrusions and the castellations get in phase and the dog gets caught by the distal edge of the respectively nearest castellation in proximal direction. The injection will not pause immediately since the dog can only stop at these edges so the respective amount of medicament will still be injected or leak out of the needle tip if the auto-injector is removed from the injection site. However, this amount can be reduced by finer castellations with a shorter clearance between them.

In an alternative embodiment the shutter arm may be actuated by a pause button. When depressed, the pause button moves the shutter arm into phase with the castellations on the housing, preventing further injection, and also holds the sheath back. The user may then move the auto-injector with the needle exposed, reinsert the needle manually and release the pause button to continue the injection.

In yet another embodiment means for latching the sheath back when in the triggering position may be arranged, wherein the plunger arms are arranged to disengage the latch means when the stopper has nearly bottomed out in the syringe. When latching the sheath back, enough clearance for the shutter ramps to move through half a pitch should be left in order to keep the pause functionality by slightly reducing pressure against the injection site.

A 'make safe' button may be arranged to allow the user to release the latch and hence the sheath at will, for example if they have stopped the injection prematurely. This mechanism requires the user to insert the needle manually if they change to a second site.

The auto-injector may preferably be used for subcutaneous or intra-muscular injection, particularly for delivering one of an analgetic, an anticoagulant, insulin, an insulin derivate, heparin, Lovenox, a vaccine, a growth hormone, a peptide hormone, a protein, antibodies and complex carbohydrates.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given herein below and the accompanying drawings which are given by way of illustration only, and thus, are not limitive of the present invention, and wherein.

Corresponding parts are marked with the same reference symbols in all figures.

DETAILED DESCRIPTION

Figure 1:
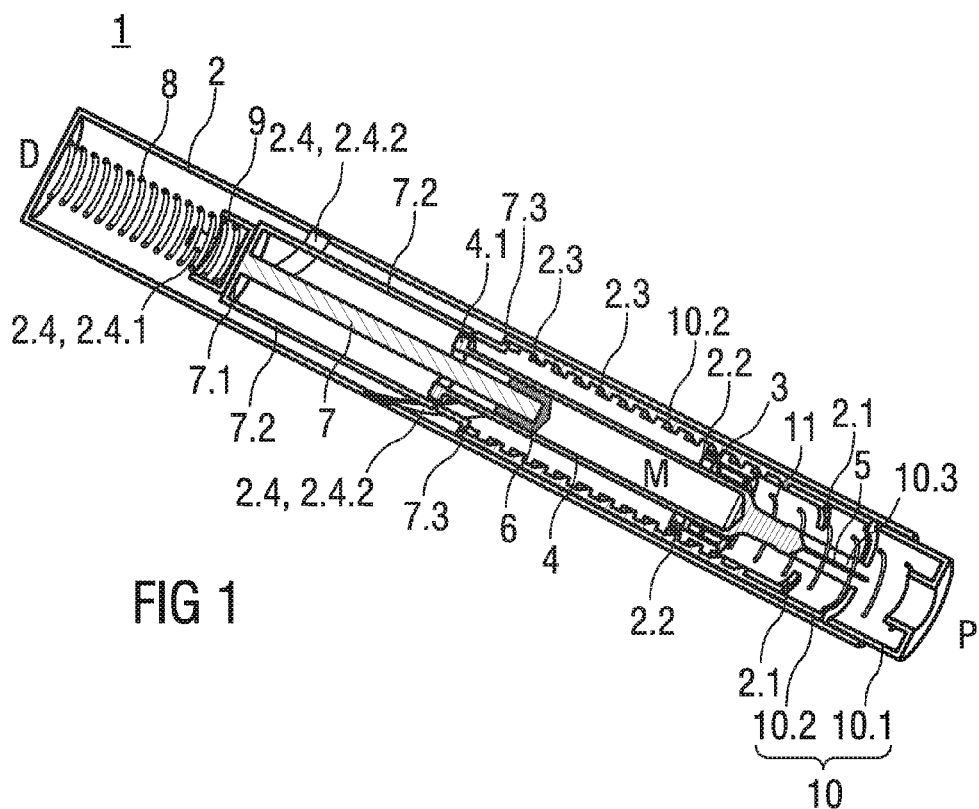
FIG. 1 is an isometric view of a longitudinal section of an auto-injector in an as delivered configuration.
Figure 2:
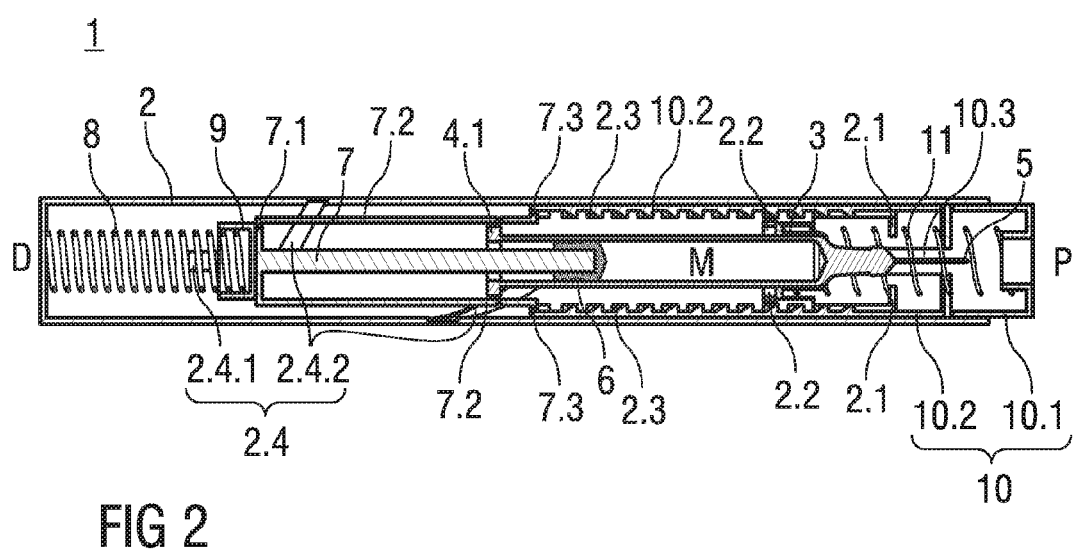
FIG. 2 is a longitudinal section of the auto-injector in the as delivered configuration.

FIG. 1 shows an isometric view of a longitudinal section of an auto-injector 1 in an as delivered configuration. FIG. 2 is a lateral view of the longitudinal section in the as delivered configuration. The auto-injector 1 comprises an elongate housing 2, which is essentially tubular with a closed distal end D and an open proximal end P. A syringe carrier 3 is arranged in the housing 2 and slidable in longitudinal direction between a proximal stop 2.1 and a distal stop 2.2 provided inside the housing 2. The syringe carrier 3 holds a syringe 4 and supports it at its proximal end in order to avoid stress to its finger flanges 4.1. A hollow injection needle 5 is attached to the proximal end of the syringe 4. A stopper 6 serves for sealing a distal end of the syringe 4. A liquid medicament M stored in the syringe 4 may be displaced through the needle 5 by pushing the stopper 6 in proximal direction P by means of a plunger 7. The plunger 7 has a thrust plate 7.1 arranged at its distal end with two or more plunger arms 7.2 extending from the edges of the thrust plate 7.1 in proximal direction P, the plunger arms 7.2 having a respective outwardly protruding dog 7.3. The plunger arms 7.2 are radially outwardly biased with respect to a longitudinal axis of the auto-injector 1.

A number of sets of longitudinal castellations 2.3 corresponding to the number of plunger arms 7.2 are arranged on the internal surface of the housing 2. Each set of castellations 2.3 consists of a number of consecutive castellations spaced from each other.

In the as delivered configuration in FIGS. 1 and 2 the dogs 7.3 of the plunger arms 7.2 abut against the most distal castellation of the respective set 2.3.

Figure 6:
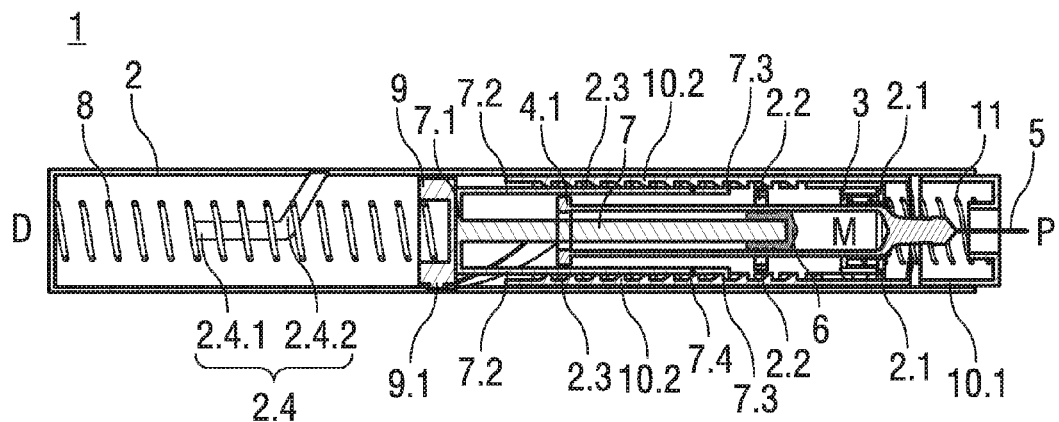
FIG. 6 is a longitudinal section of the auto-injector with the injection paused.

A drive spring 8 for inserting the injection needle 5 into an injection site, e.g. a patient's skin and for displacing the liquid medicament M from the syringe 4 through the hollow injection needle 5 is arranged near the distal end D of the auto-injector 1 inside the housing 2. The distal end of the drive spring 8 is grounded in the housing 2. The proximal end of the drive spring 8 bears against a cup-shaped rotating damper 9 which in turn bears against the distal side of the thrust plate 7.1. The rotating damper 9 has a cam 9.1 (see FIGS. 4 and 6) which is guided in a cam track 2.4 on the inner surface of the housing 2.

A sheath 10.1 of a sheath arrangement 10 is telescoped within the proximal end of the housing 2. The sheath arrangement 10 comprises the essentially tubular sheath 10.1 and a number of shutter arms 10.2 corresponding to the number of sets of castellations 2.3 in the housing 2 and extending in distal direction D from the sheath 10.1 alongside the respective sets of castellations 2.3. Each shutter arm 10.2 has a number of consecutive ramped protrusions spaced from each other. The pitch between the ramped protrusions equals the pitch between the castellations of the respective castellation sets 2.3. A sheath spring 11 is arranged so as to bias the sheath 10.1 against the syringe carrier 3.

The sheath 10.1 is prevented from moving out of the housing 2 by a sheath arm 10.3 extending distally from the sheath 10.1 and engaged behind the distal side of the syringe carrier 3 (not illustrated).

In the configuration as delivered the drive spring 8 is held in a compressed state between the distal end of the housing 2 and the rotating damper 9. The plunger 7 cannot be pushed in proximal direction P because of the plunger arms 7.2 caught behind the most distal castellation.

In FIGS. 1 and 2 the syringe 4 is held by the syringe carrier 3 which is prevented from moving by one or more clips on the case (not illustrated). There may be an aperture or a recess in the case where the clip is engaged in. The clip may be disengaged from the recess by a feature on the sheath arm 10.3.

The needle 5 is covered inside the housing 2 and the sheath 10.1 thus preventing a user from finger-stick injuries.

Figure 3:
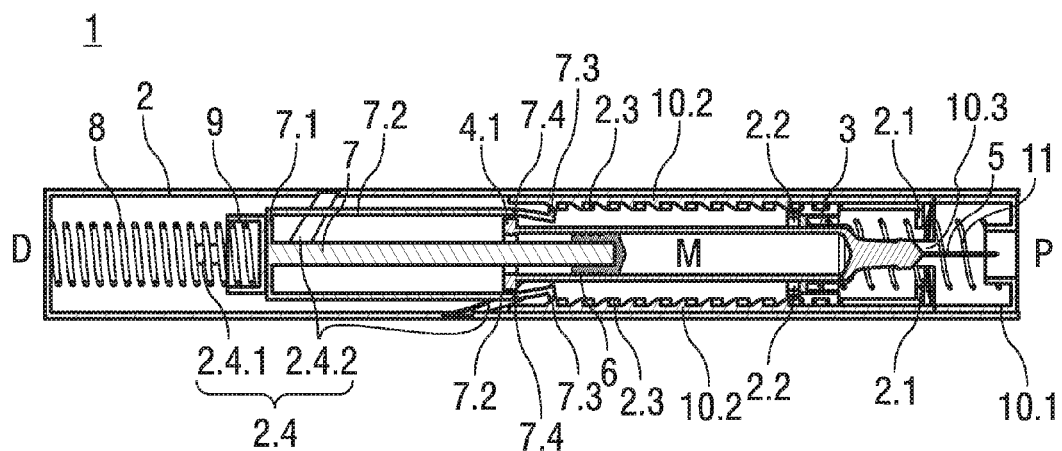
FIG. 3 is a longitudinal section of the triggered auto-injector.

In order to trigger the auto-injector 1 its proximal end with the sheath 10.1 must be pushed against the injection site. Thereby the sheath 10.1 is moved in distal direction D into the housing 2 against the load of the sheath spring 11. The shutter arms 10.2 are also moved in distal direction D until the most distal ramped protrusion meets the respective dog 7.3 on the plunger arm 7.2. At this point in the axial motion of the sheath 10.1 the sheath arm 10.3 has released the clips between the syringe carrier 3 and the housing 2 so the syringe carrier 3 and syringe 4 may translate in proximal direction D. However, this is prevented by the relatively weak force of the sheath spring 11 in this situation. If the auto-injector 1 is removed from the injection site at this point the sheath arrangement 10 returns to the position shown in FIGS. 1 and 2 under the load of the sheath spring 11 and the clip re-engages the syringe carrier 3 with the housing 2. If the auto-injector 1 is pushed further, as illustrated in FIG. 3, the dogs 7.3 of the plunger arms 7.2 are pushed inwardly thus resiliently deforming the ends of the plunger arms 7.2. In order to do this the user has to exert an increased force on the sheath 10.1, in other words there is a step in required force level thus providing a two stage triggering of the auto-injector 1. In the illustrated embodiment the proximal ends of the plunger arms 7.2 are bent around the finger flange 4.1 of the syringe 4 so the force required to do this is higher because of the relatively short lever formed by the plunger arm 7.2 between the finger flange 4.1 and the dog 7.3. An indent 7.4 is provided outwardly in the plunger arm 7.2 so as to be at a level with the finger flange 4.1 in the configuration as delivered. The indent 7.4 provides a defined resilience of the plunger arms 7.2 and thus a defined force for bending them inwards.

When the ramped protrusion has pushed the dog 7.3 inwards (see FIG. 3) the dog 7.3 is no longer engaged with the most distal castellation of the set 2.3 so the plunger 7 may be translated in proximal direction P. The compressed drive spring 8 pushes the rotating damper 9, the plunger 7 and the stopper 6 in proximal direction P. The force of the sheath spring 11 in this situation has to be greater than a counteracting force of the stopper 6 due to friction between the stopper 6 and the inner wall of the syringe 4 and due to the hydrostatic resistance of the liquid medicament M to be displaced through the hollow needle 5. Therefore, the sheath spring 11 is compressed and the syringe carrier 3 travels in proximal direction P together with the syringe 4 and the needle 5. Hence, the needle 5 is inserted into the injection site. The injection depth is controlled by the syringe carrier hitting the proximal stop 2.1 on the housing 2. From this point on the syringe 4 is no longer forwarded. Instead the stopper 6 is translated by the expanding drive spring 8 in proximal direction P within the syringe 4 thus ejecting the medicament M through the needle 5 into the injection site.

Figure 5:
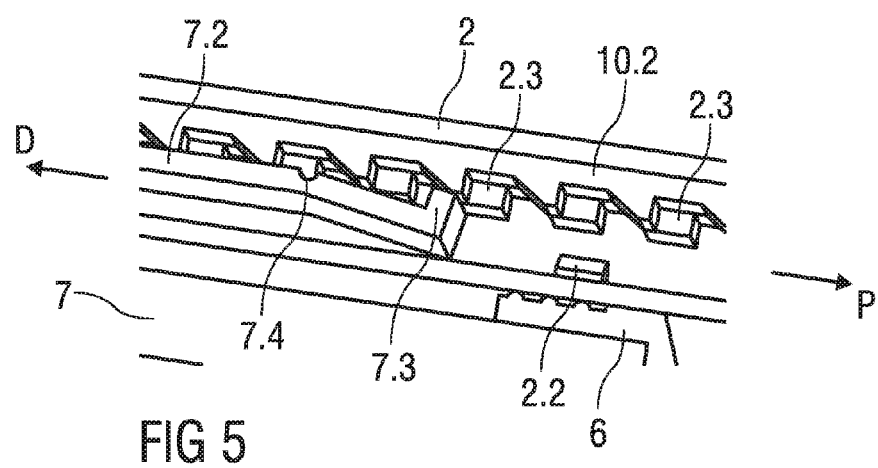
FIG. 5 is a detail view of a set of castellations in the situation illustrated in FIG. 4.

As the drive spring 8 expands, the plunger arms 7.2 slide over the surface provided by a combination of the castellations of a set 2.3 and the ramped protrusions of the shutter arms 10.2 which are staggered in an unlocking position in such a manner that the ramped protrusions of the shutter arms 10.2 are out of phase with the castellations or at least nearly in phase with the spaces between the castellations of a set 2.3 (cf. FIG. 5).

Throughout the translation in proximal direction P, the rotating damper 9 follows the cam track 2.4. This provides a controllable friction force between the rotating damper 9 and the thrust plate 7.1 of the plunger 7 which cannot rotate as it is keyed into the housing 2. The cam track 2.4 can be specified to control the speed of needle insertion and drug delivery. In the embodiment shown the cam track 2.4 comprises a straight section 2.4.1 in parallel to the longitudinal axis of the auto-injector 1. During needle insertion the cam 9.1 of the rotating damper 9 is guided along this straight section 2.4.1 so the rotating damper 9 does not rotate and the power of the drive spring 8 is entirely forwarded to the plunger 7. When the needle 5 has reached its injection depth the cam 9.1 of the rotating damper 9 enters a helical section 2.4.2 of the cam track 2.4. This causes the rotating damper 9 to rotate when being translated further. Hence the load of the drive spring 8 is split between the plunger 7 and the friction force generated by the rotation of the rotating damper 9 on the thrust plate 7.1 providing a slower injection. Fast needle insertion and slow injection is thought to be less painful for a patient.

Figure 4:
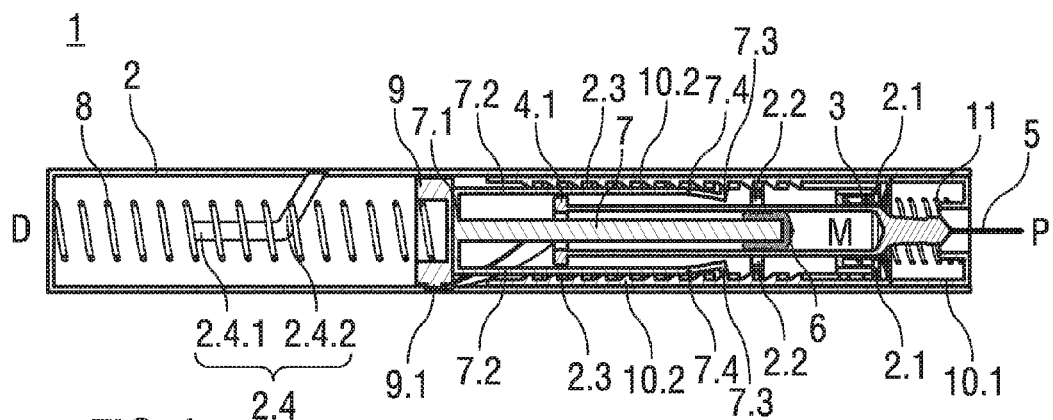
FIG. 4 is a longitudinal section of the auto-injector during an injection.

FIG. 4 is a longitudinal section of the auto-injector 1 during the injection. FIG. 5 is a detail view of the set of castellations 2.3 in the situation illustrated in FIG. 4.

The user may pause the delivery of the medicament M by reducing the pressure on the sheath 10.1, whereby the shutter arms 10.2 move in proximal direction P into a locking position with the ramped protrusions essentially in phase with the castellations. This changes the profile of the surface consisting of the set 2.3 of castellations and the ramped protrusions of the shutter arms 10.2 in such a manner that a distal edge of the castellations is being exposed so the plunger arms 7.1 may flex outwards and get caught behind one of these edges thus interrupting the injection. If the user increases the pressure on the sheath 10.1 once more the ramped protrusion will push the plunger arm 7.1 inwards again until it comes clear of the protrusion so the injection continues. In the embodiment shown it would not be possible to restart the injection if the auto-injector 1 were completely removed from the injection site.

Figure 7:
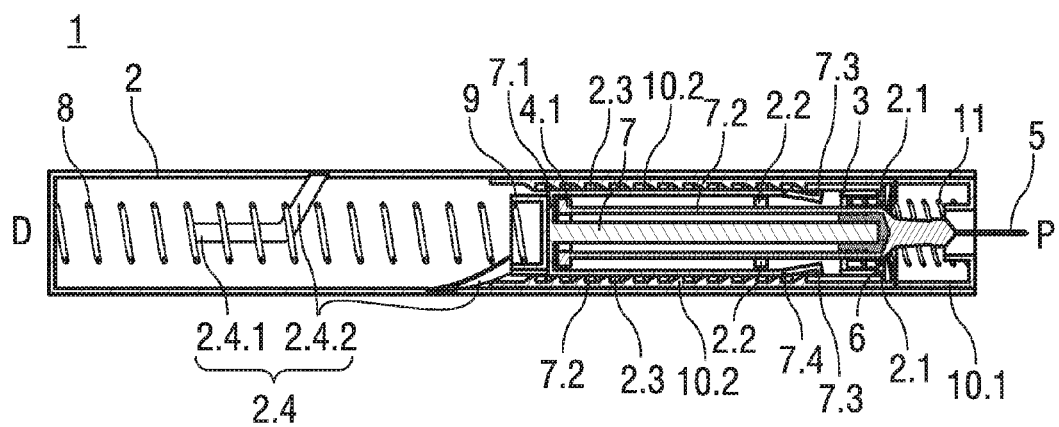
FIG. 7 is a longitudinal section of the auto-injector at the end of injection.

In FIG. 7 the auto-injector 1 is shown at the end of injection. The stopper 6 has bottomed out in the syringe 4 and the medicament M has been at least almost entirely been ejected from the syringe 4.

Figure 8:
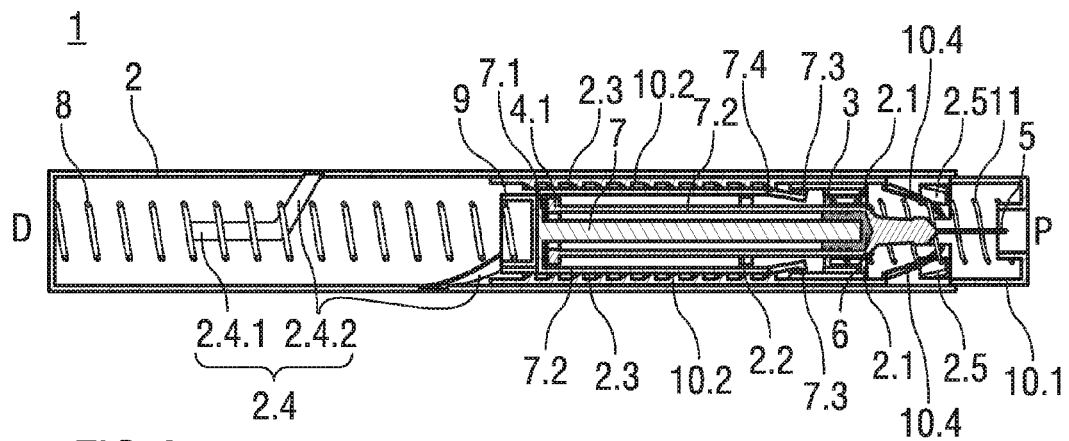
FIG. 8 is a longitudinal view of the auto-injector after the end of injection with an advanced needle shroud.

As the user removes the auto-injector 1 from the injection site, the sheath 10.1 moves in proximal direction P due to the force of the sheath spring 11 which was compressed by the drive spring 8 during needle insertion (see FIG. 8). When the sheath 10.1 is far enough moved in proximal direction P to protect the user from the needle 5, snaps 2.5 on the proximal end of the housing 2 move inwards permanently thus preventing the sheath 10.1 from moving back into the housing 2.

In the embodiment illustrated in FIG. 8 the sheath arrangement 10 comprises two or more resilient beams 10.4 which link the sheath 10.1 to the shutter arms 10.2 in a manner to allow the sheath 10.1 to be moved away from the shutter arms 10.2 so sheath 10.1 can be moved even if the shutter arms 10.2 are caught on the plunger arms 7.2 as is the case if the auto-injector 1 is removed from the injection site prematurely, i.e. before the entire dose has been ejected.

The sheath 10.1 cannot move further beyond the proximal end P of the auto-injector 1 as the sheath arm 10.3 is latched to the syringe carrier 3.

In an alternative embodiment of the invention the sheath 10.1 and the shutter arms 10.2 may be manufactured as separate parts.

In an alternative embodiment an intermediary component may be provided for first coupling the plunger 7 to the syringe carrier 3 or the syringe 4 directly without acting on the stopper 6 until the needle 5 has reached its injection depth. The plunger 7 would then be decoupled from the syringe 4 or syringe carrier 3 by the intermediary component and instead be coupled to the stopper 6 in order to displace the medicament M from the syringe 4. Thus, wet injection is avoided, i.e. the medicament M is not leaking out of the needle tip before the needle 5 is inserted.

In another alternative embodiment the auto-injector 1 may be designed to allow the injection to be paused, the auto-injector removed from the injection site, moved to another site and the injection continued, i.e. split dose use. This may be achieved by one of the following options (not illustrated):

The ramped shutter arm 10.2 may be made as a separate component from the sheath 10.1 and may be actuated by a pause button. When depressed, the pause button moves the shutter arms 10.2 in phase, preventing further injection, and also holds the sheath 10.1 back. The user may then move the auto-injector 1 with the needle 5 exposed, reinsert the needle 5 manually and release the pause button to continue the injection. If the pause button is not depressed, functionality does not differ from that described in the illustrated embodiments.

The sheath 10.1 may be latched back on triggering, leaving enough clearance for the shutter ramps to move through half a pitch if the auto-injector 1 is subsequently removed from the injection site, thereby causing the injection to 'pause' and leaving the needle exposed. This mechanism requires the user to insert the needle 5 manually if they change to a second site. Immediately prior to the stopper 6 reaching the end of the syringe 4, the plunger 7 releases the latch, and sheath 10.1 is freed to move to a fully proximal position, shielding the needle. Additionally a 'make safe' button allows the user to release the latch and hence the sheath 10.1 at will, for example if they have stopped the injection prematurely. The sheath 10.1 will then latch in the fully proximal position by means of the snaps 2.5 when the device is removed from the injection site A more complex design may allow the auto-injector to be 're-cocked' and hence automatically insert the same needle 5 in different injection sites. An implementation of this may be a sleeve over the outside of the auto-injector 1 which can be slid towards the user for latching both the syringe carrier 3 and the plunger 7 through a slot in the housing 2. The auto-injector 1 can then be removed from the injection site, the outer sleeve pulled in distal direction D (moving the plunger control surfaces to an earlier castellation) and the auto-injector 1 can be reused with the rest of the dose. In order to allow the plunger arms 7.2 to move in distal direction D, the castellations may be changed to ramps facing in the opposite direction of the shutter ramps.

In yet another alternative embodiment the pause functionality may be removed by modifying the profile of the shutter ramps and castellations.

The invention claimed is:

1. A shuttering mechanism for controlling translation of a longitudinally moveable component within an elongate housing, the shuttering mechanism comprising:
   a plurality of castellations longitudinally disposed on the housing; and
   at least one resilient arm associated with the longitudinally moveable component, the resilient arm having a dog resiliently biased towards the castellations, the dog adapted to engage between or behind the castellations and block the translation of the longitudinally moveable component,
   wherein a respective shutter arm is arranged alongside the plurality of castellations, the shutter arm having a plurality of consecutive ramped protrusions spaced from each other,
   wherein the castellations and the ramped protrusions have the same pitch,
   wherein a profiled surface is formed by the castellations and the ramped protrusions,
   wherein the shutter arm is moveable in a longitudinal direction with respect to the plurality of castellations, and
   wherein the shutter arm has at least one locking position with its ramped protrusions essentially in phase with the castellations thus allowing the dog of the resilient arm to catch between or behind the castellations and wherein the shutter arm has at least one unlocking position with its ramped protrusions out of phase with the castellations in such a manner that the ramped protrusions prevent the dog from engaging with the castellations or disengage them thus allowing translation of the longitudinally moveable component.

2. An auto-injector for administering a dose of a liquid medicament, the auto-injector having a distal end and a proximal end with an orifice intended to be applied against an injection site, the auto-injector comprising:
   an elongate housing arranged to contain a syringe with a hollow needle and a stopper for sealing the syringe and displacing the medicament, wherein the syringe is slidably arranged with respect to the housing,
   a drive mechanism capable of, upon activation:
      pushing the needle from a retracted position into an advanced position through the orifice and past the proximal end, and
      operating the syringe to supply the dose of medicament,
   a plunger for transmitting power from the drive mechanism to the syringe and/or stopper, and
   a shuttering mechanism arranged to lock the drive mechanism in a compressed state prior to manual operation and capable of, upon manual operation, releasing the drive mechanism for injection,
   wherein the shuttering mechanism comprises a plurality of castellations longitudinally disposed on the housing, and at least one plunger arm attached to the plunger, the plunger arm having a dog resiliently biased towards the castellations, the dog adapted so as to engage between or behind the castellations and block the translation of the plunger,
   wherein a respective shutter arm is arranged alongside the plurality of castellations, the shutter arm having a number plurality of consecutive ramped protrusions spaced from each other, wherein the shutter arm is moveable in a longitudinal direction with respect to the plurality of castellations,
   wherein the shutter arm has at least one locking position with its ramped protrusions essentially in phase with the castellations thus allowing the dog of the plunger arm to catch between or behind the castellations and
   wherein the shutter arm has at least one unlocking position with its ramped protrusions out of phase with the castellations in such a manner that the ramped protrusions prevent the dog from engaging with the castellations or disengage them thus allowing translation of the plunger.

3. The auto-injector according to claim 2, wherein the shutter arm of the shuttering mechanism is: (i) connected to a sheath, (ii) telescoped within the proximal end of the housing, and (iii) arranged to protrude proximally from the housing at least in an initial position in an as-delivered state of the auto-injector with the shutter arm in the locking position, wherein translating the sheath in a proximal direction into a triggering position shifts the shutter arm into the unlocking position.

4. The auto-injector according to claim 3, further including a syringe carrier arranged inside the housing for holding the syringe, the syringe carrier being slidable with respect to the housing, wherein the syringe carrier comprises at least one clip locking the syringe carrier to the housing in a distal position, in order to prevent axial motion of the syringe carrier relative to the housing, wherein the sheath is arranged to disengage the clip upon translation in the proximal direction before the shutter arm reaches its unlocking position thus allowing the syringe carrier to move in the proximal direction.

5. The auto-injector according to claim 3, wherein the sheath and the shutter arms are connected by at least one resilient beam, a manner to allow the sheath to be moved away from the shutter arms by a defined maximum distance.

6. The auto-injector according to claim 3, wherein the sheath is biased in a proximal direction by a sheath spring.

7. The auto-injector according to claim 6, wherein the sheath spring is arranged to bias the sheath against the syringe carrier.

8. The auto-injector according to claim 6, wherein the sheath is engaged with the syringe carrier in a manner to allow a maximum distance between the sheath and the syringe carrier so that a maximum proximal position of the sheath is restricted by the longitudinal position of the syringe carrier thus allowing the sheath to move proximally beyond its initial position if the syringe carrier is proximal from is distal position.

9. The auto-injector according to claim 3, wherein at least one snap is provided near the proximal end of the housing, for preventing the sheath from moving in distal direction when the sheath has moved into a locking position proximally from its initial position.

10. The auto-injector according to claim 2, wherein the drive mechanism is a compression spring grounded distally in the housing and bearing against the plunger.

11. The auto-injector according to claim 10, wherein a rotating damper is arranged between the compression spring and a thrust plate at a distal end of the plunger, wherein a cam of the rotating damper is arranged in a cam track on an inner surface of the housing, the cam track having at least one helical section for forcing the rotating damper to rotate upon axial translation under load of the compression spring thus generating friction between the rotating damper and the thrust plate.

12. The auto-injector according to claim 11, wherein the cam track has a straight section for preventing rotation of the rotating damper during needle insertion.

13. The auto-injector according to claim 2, further including a pause button adapted to actuate the shutter arm.

14. The auto-injector according to claim 3, further including a latch mechanism adapted to hold the sheath back when in the triggering position, wherein the plunger arms are arranged to disengage the latch mechanism when the stopper has nearly bottomed out in the syringe.

15. The auto-injector according to claim 14, further including a button arranged for disengaging the latch mechanism.

* * * * *